(12) United States Patent
Sampietro et al.

(10) Patent No.: US 11,071,724 B2
(45) Date of Patent: Jul. 27, 2021

(54) COMPOSITIONS AND METHODS FOR TREATING PRESBYOPIA

(71) Applicant: Ocular Science, Inc., Manhattan Beach, CA (US)

(72) Inventors: Anthony Sampietro, Hermosa Beach, CA (US); Damien Goldberg, Manhattan Beach, CA (US); Amy Frost, Stevensville, MT (US); Brian Holdorf, Missoula, MT (US)

(73) Assignee: OCULAR SCIENCE, INC., Manhattan Beach, CA (US)

( * ) Notice: Subject to any disclaimer, the term of this patent is extended or adjusted under 35 U.S.C. 154(b) by 50 days.

(21) Appl. No.: 16/590,830

(22) Filed: Oct. 2, 2019

(65) Prior Publication Data

US 2020/0360346 A1 Nov. 19, 2020

Related U.S. Application Data (60) Provisional application No. 62/849,728, filed on May 17, 2019.

(51) Int. Cl.
| | |
|---|---|
| *A61K 31/4402* | (2006.01) |
| *C07D 213/38* | (2006.01) |
| *A61K 31/4178* | (2006.01) |
| *A61K 31/135* | (2006.01) |
| *A61K 31/44* | (2006.01) |
| *A61K 31/407* | (2006.01) |
| *A61K 9/00* | (2006.01) |
| *A61K 47/10* | (2017.01) |
| *A61K 47/18* | (2017.01) |
| *A61K 47/34* | (2017.01) |
| *A61K 47/02* | (2006.01) |

(52) U.S. Cl.
CPC ........ *A61K 31/4178* (2013.01); *A61K 9/0048* (2013.01); *A61K 31/135* (2013.01); *A61K 31/407* (2013.01); *A61K 31/44* (2013.01); *A61K 47/02* (2013.01); *A61K 47/10* (2013.01); *A61K 47/186* (2013.01); *A61K 47/34* (2013.01)

(58) Field of Classification Search
CPC .......................... A61K 31/4402; C07D 213/38
USPC ......................................... 514/357; 546/329
See application file for complete search history.

(56) References Cited

U.S. PATENT DOCUMENTS

| | | | |
|---|---|---|---|
| 5,811,446 A | 9/1998 | Thomas | |
| 6,372,254 B1 | 4/2002 | Ting | |
| 6,548,079 B1 | 4/2003 | Kuhn | |
| 6,551,584 B2 | 4/2003 | Bandyopadhyay | |
| 6,716,830 B2 | 4/2004 | Cagle | |
| 6,730,321 B2 | 5/2004 | Ting | |
| 6,740,664 B2 | 5/2004 | Cagle | |
| 7,612,115 B2 | 11/2009 | Suzuki | |
| 7,799,337 B2 | 9/2010 | Levin | |
| 7,971,070 B2 | 6/2011 | Lotspiech et al. | |
| 8,173,707 B2 | 5/2012 | Demopulos | |
| 8,263,125 B2 | 9/2012 | Vaya | |
| 8,268,352 B2 | 9/2012 | Vaya | |
| 8,470,784 B2 | 6/2013 | Liu | |
| 8,586,633 B2 | 11/2013 | Demopulos | |
| 8,680,078 B2 | 3/2014 | Aleo | |
| 8,778,999 B2 | 7/2014 | Hosseini | |
| 9,016,221 B2 | 4/2015 | Brennan | |
| 9,066,856 B2 | 6/2015 | Demopulos | |
| 9,087,145 B2 | 7/2015 | Ballou | |
| 9,271,866 B2 | 3/2016 | Humayun | |
| 9,278,101 B2 | 3/2016 | Demopulos | |
| 9,308,124 B2 | 4/2016 | Humayun | |
| 9,399,040 B2 | 7/2016 | Demopulos | |
| 9,486,406 B2 | 11/2016 | Demopulos | |
| 9,554,968 B2 | 1/2017 | Weikart | |
| 9,585,895 B2 | 3/2017 | Demopulos | |
| 9,662,450 B2 | 5/2017 | Jones | |
| 9,855,246 B2 | 1/2018 | Demopulos | |
| 10,016,338 B2 | 7/2018 | Weikart | |
| 10,285,957 B2 | 5/2019 | Karolchyk | |
| 2002/0035264 A1 | 3/2002 | Kararli | |
| 2004/0072809 A1 | 4/2004 | Demopulos | |
| 2005/0043214 A1 | 2/2005 | Goerne | |

(Continued)

FOREIGN PATENT DOCUMENTS

WO WO2017192675 11/2017

OTHER PUBLICATIONS

Marx et al. Ophthalmic Squeeze Dispenser (OSD): Does One Size Fit All? Drug Development and Delivery. Available at https://drug-dev.com/primary-packaging-ophthalmic-squeeze-dispenser-osd-does-one-size-fit-all/ (Oct. 1, 2015).

(Continued)

*Primary Examiner* — Douglas M Willis (74) *Attorney, Agent, or Firm* — Wilson Sonsini Goodrich & Rosati (57) ABSTRACT

Compositions for treating presbyopia may include active pharmaceutical ingredients of pilocarpine HCl, phenylephrine HCl, pheniramine maleate, and ketorolac tromethamine. Other ingredients may include boric acid, polyethylene glycol, propylene glycol, and BAK (benzalkonium chloride). The pilocarpine HCl may be in a range of 0.1% to 2%. The phenylephrine HCl may be in a range of 0.1% to 1.5%. The pheniramine maleate may be in a range of 0.07% to 0.35%. The ketorolac tromethamine may be in a range of 0.01% to 0.6%. The boric acid may be in a range of 0.5% to 1.5%. The polyethylene glycol may be in a range of 0.1% to 1%. The propylene glycol may be in a range of 0.1% to 1%. The BAK may be in a range of 0.005% to 0.01%. The solvent may be mostly water.

15 Claims, 8 Drawing Sheets

(56) References Cited

U.S. PATENT DOCUMENTS

| | | |
|---|---|---|
| 2005/0261641 A1 | 11/2005 | Warchol |
| 2006/0183698 A1 | 8/2006 | Abelson |
| 2007/0211212 A1 | 9/2007 | Bennwik |
| 2009/0048261 A1 | 2/2009 | Tornero Montano |
| 2009/0069345 A1 | 3/2009 | Tornero Montano |
| 2010/0063017 A1 | 3/2010 | Rajan |
| 2010/0105643 A1 | 4/2010 | Soll |
| 2010/0227928 A1 | 9/2010 | Hosseini |
| 2010/0311705 A1 | 12/2010 | Demopulos |
| 2011/0178147 A1 | 7/2011 | Likitlersuang et al. |
| 2011/0294768 A1 | 12/2011 | Rajan |
| 2012/0184552 A1 | 7/2012 | Nakajima |
| 2012/0316143 A1 | 12/2012 | Soll |
| 2013/0020227 A1 | 1/2013 | Stack |
| 2013/0035338 A1 | 2/2013 | Tang |
| 2013/0041241 A1 | 2/2013 | Felts |
| 2013/0065869 A1 | 3/2013 | Demopulos |
| 2013/0079344 A1 | 3/2013 | Demopulos |
| 2013/0165419 A1 | 6/2013 | Lindstrom |
| 2013/0338126 A1 | 12/2013 | Rajan |
| 2014/0024642 A1 | 1/2014 | Vejarano Restrepo |
| 2014/0036225 A1 | 2/2014 | Chehab et al. |
| 2014/0187497 A1 | 7/2014 | Jacob |
| 2014/0213561 A1 | 7/2014 | Rajan |
| 2014/0221326 A1 | 8/2014 | Demopulos |
| 2014/0235597 A1 | 8/2014 | Demopulos |
| 2015/0024996 A1 | 1/2015 | Liegner |
| 2015/0025511 A1 | 1/2015 | Wiley |
| 2015/0119440 A1 | 4/2015 | Karolchyk |
| 2015/0129457 A1 | 5/2015 | Flodin |
| 2015/0164882 A1 | 6/2015 | Dilzer |
| 2015/0335704 A1 | 11/2015 | Karolchyk |
| 2016/0101118 A1 | 4/2016 | Fernandez |
| 2016/0101178 A1 | 4/2016 | Wilson |
| 2016/0106761 A1 | 4/2016 | Demopulos |
| 2016/0175323 A1 | 6/2016 | Wiley |
| 2016/0184323 A1 | 6/2016 | Wiley |
| 2016/0243031 A1 | 8/2016 | Wiley |
| 2016/0279055 A1 | 9/2016 | Liegner |
| 2016/0354308 A1 | 12/2016 | Karolchyk |
| 2017/0049721 A1 | 2/2017 | Karolchyk |
| 2017/0100412 A1 | 4/2017 | Demopulos |
| 2017/0312295 A1 | 11/2017 | Demopulos |
| 2018/0055790 A1 | 3/2018 | Karolchyk |
| 2018/0147214 A1 | 5/2018 | Ostrow et al. |
| 2019/0008832 A1 | 1/2019 | Pinelli |
| 2019/0105320 A1 | 4/2019 | Fernandez |
| 2019/0111045 A1 | 4/2019 | Wiley |

OTHER PUBLICATIONS

PCT/US2020/042414 International Search Report and Written Opinion dated Oct. 16, 2020.

FIG. 1

| BROWN color pupils | EYE | UCDNVA | PUPIL SIZE | COMMENTS | AGE |
|---|---|---|---|---|---|
| H0 (drops placed) | OD | J2 | 3.42 | | 46 |
| | OS | J3 | 4.07 | | |
| Hour 1 (H1) | OD | J1+ | 3.31 | eye muscle feels like its working | |
| | OS | J1+ | 3.61 | | |
| Hour 3 (H3) (drops placed) | OD | J1+ | 3.21 | | |
| | OS | J1+ | 3.51 | | |
| Hour 5 (H5) | OD | J2 | 3.01 | | |
| | OS | J2 | 3.33 | | |
| Hour 8 (H8) | OD | J3 | 3.89 | | |
| | OS | J3 | 4 | | |
| Day 2 | EYE | UCDNVA | PUPIL SIZE | COMMENTS | AGE |
| H0 (drops placed) | OD | J2 | 3.59 | | 46 |
| | OS | J3 | 4 | | |
| H1 | OD | J1+ | 3.22 | | |
| | OS | J1+ | 3.88 | | |
| H3 | OD | J1 | 3.11 | | |
| | OS | J1 | 3.26 | | |
| H5 | OD | J2 | 2.99 | | |
| | OS | J2 | 3 | | |
| H8 | OD | J3 | 3.16 | | |
| | OS | J3 | 3.34 | | |

FIG. 2

| HAZEL | EYE | UCDNVA | PUPIL SIZE | COMMENTS | AGE |
|---|---|---|---|---|---|
| H0 (drop placed) | OD | J2 | 4.06 | | 53 |
| | OS | J3 | 3.8 | | |
| H1 | OD | J1 | 3 | dark surroundings, slight brow discomfort | |
| | OS | J1 | 3.06 | | |
| H3 | OD | J1 | 3.35 | | |
| | OS | J1 | 3.96 | | |
| H5 | OD | J1 | 3.01 | | |
| | OS | J2 | 3.45 | | |
| H8 | OD | J2 | 3.22 | | |
| | OS | J2 | 3.66 | | |
| Day 2 | EYE | UCDNVA | PUPIL SIZE | COMMENTS | AGE |
| H0 (drops placed) | OD | J2 | 4.04 | | 53 |
| | OS | J3 | 4.95 | | |
| H1 | OD | J1 | 3.11 | | |
| | OS | J2 | 3.22 | | |
| H3 (drops placed) | OD | J1 | 3.66 | | |
| | OS | J2 | 3.55 | | |
| H5 | OD | J1 | 2.65 | dark surroundings | |
| | OS | J2 | 2.69 | slight brow discomfort | |
| H8 | OD | J2 | 3 | | |
| | OS | J2 | 3.05 | | |

FIG. 3

| HAZEL | EYE | UCDNVA | PUPIL SIZE | COMMENTS | AGE |
|---|---|---|---|---|---|
| H0 (drops placed) | OD | J10 | 3.01 | | 53 |
| | OS | J5 | 2.73 | | |
| H1 | OD | J5 | 1.88 | slight brow discomfort | |
| | OS | J3 | 1.7 | | |
| H3 (drops placed) | OD | J2 | 1.65 | | |
| | OS | J2 | 1.64 | | |
| H5 | OD | J2 | 2 | | |
| | OS | J2 | 2.13 | | |
| H8 | OD | J3 | 2.45 | | |
| | OS | J5 | 3 | | |
| Day 2 | EYE | UCDNVA | PUPIL SIZE | COMMENTS | AGE |
| H0 (drops placed) | OD | J8 | 3.57 | | 53 |
| | OS | J8 | 3.16 | | |
| H1 | OD | J5 | 1.95 | | |
| | OS | J5 | 1.84 | | |
| H3 | OD | J2 | 1.66 | | |
| | OS | J2 | 1.77 | | |
| H5 | OD | J1 | 2.73 | | |
| | OS | J1 | 2.66 | | |
| H8 | OD | J2 | 3.12 | | |
| | OS | J2 | 3.33 | | |

FIG. 4

| BROWN | EYE | UCDNVA | PUPIL SIZE | COMMENTS | AGE |
|---|---|---|---|---|---|
| H0 (drops placed) | OD | J2 | 4.75 | | 44 |
| | OS | J2 | 4.55 | | |
| H1 | OD | J1 | 4.1 | | |
| | OS | J1 | 4.12 | | |
| H3 (drops placed) | OD | J1 | 4.89 | | |
| | OS | J1 | 4.77 | | |
| H5 | OD | J2 | 4.03 | | |
| | OS | J2 | 3.69 | | |
| H8 | OD | J2 | 4.54 | | |
| | OS | J2 | 4.74 | | |
| Day 2 | EYE | UCDNVA | PUPIL SIZE | COMMENTS | AGE |
| H0 (drops placed) | OD | J3 | 4.65 | | 44 |
| | OS | J2 | 4.6 | | |
| H1 | OD | J1 | 4 | | |
| | OS | J1 | 3.88 | | |
| H 3 | OD | J1 | 3.55 | | |
| | OS | J1 | 3.13 | | |
| H 5 | OD | J1 | 4.12 | | |
| | OS | J1 | 4 | | |
| H8 | OD | J2 | 4.55 | | |
| | OS | J2 | 4.72 | | |

FIG. 5

| HAZEL | EYE | UCDNVA | PUPIL SIZE | COMMENTS | AGE |
|---|---|---|---|---|---|
| H0 (drops placed) | OD | J10 | 5.11 | reading add +2.50 | 62 |
|  | OS | J10 | 4.74 |  |  |
| H1 | OD | J5 | 2.43 | dark surroundings |  |
|  | OS | J5 | 2.74 |  |  |
| H3 (drops placed) | OD | J5 | 3.54 |  |  |
|  | OS | J5 | 3.68 |  |  |
| H5 | OD | J3 | 3.77 |  |  |
|  | OS | J3 | 3.89 |  |  |
| H8 | OD | J5 | 3.99 |  |  |
|  | OS | J5 | 4.02 |  |  |
| Day 2 | EYE | UCDNVA | PUPIL SIZE | COMMENTS | AGE |
| H0 (drops placed) | OD | J10 | 5.22 |  | 62 |
|  | OS | J10 | 5.1 |  |  |
| H1 | OD | J5 | 3 | dark surroundings |  |
|  | OS | J3 | 3.12 |  |  |
| H 3 | OD | J5 | 2.89 |  |  |
|  | OS | J5 | 2.77 |  |  |
| H5 | OD | J3 | 2.59 |  |  |
|  | OS | J3 | 2.14 |  |  |
| H8 | OD | J3 | 3.88 |  |  |
|  | OS | J3 | 3.14 |  |  |

FIG. 6

| BROWN | EYE | UCDNVA | PUPIL SIZE | COMMENTS | AGE |
|---|---|---|---|---|---|
| H0 (drops placed) | OD | J1 | 5.5 | | 46 |
| | OS | J1 | 5.5 | | |
| H1 | OD | J1 | 5 | headache | |
| | OS | J1 | 5 | | |
| H3 (drops placed) | OD | J1 | 3.5 | headache, paid around eye | |
| | OS | J1+ | 2 | | |
| H5 | OD | J1 | 4.5 | headache, paid around eye | |
| | OS | J1 | 3 | | |
| H8 | OD | J1 | 5 | | |
| | OS | J1 | 4 | | |

FIG. 7

| BROWN | EYE | UCDNVA | PUPIL SIZE | COMMENTS | AGE |
|---|---|---|---|---|---|
| H0 (drops placed) | OD | J5 | 4 | none | 47 |
| | OS | J5 | 4 | | |
| H1 | OD | J4 | 4 | | |
| | OS | J4 | 4 | | |
| H3 (drops placed) | OD | J3 | 3 | | |
| | OS | J3 | 3 | | |
| H5 | OD | J3 | 3.5 | | |
| | OS | J3 | 3.5 | | |
| H8 | OD | J4 | 4 | | |
| | OS | J4 | 4 | | |

FIG. 8

| BROWN | EYE | UCDNVA | PUPIL SIZE | COMMENTS | AGE |
|---|---|---|---|---|---|
| H0 (drops placed) | OD | J10 | 4 | pseudophakia OU | 64 |
| | OS | J5 | 4 | | |
| H1 | OD | J10 | 4 | | |
| | OS | J5 | 4 | | |
| H3 (drops placed) | OD | J8 | 3 | headache | |
| | OS | J5 | 3 | | |
| H5 | OD | J8 | 3 | headache | |
| | OS | J5 | 3 | | |
| H8 | OD | J8 | 3 | headache | |
| | OS | J5 | 3 | | |

FIG. 9

| BROWN | EYE | UCDNVA | PUPIL SIZE | COMMENTS | AGE |
|---|---|---|---|---|---|
| H0 (drops placed) | OD | J3 | 4 | none | 64 |
| | OS | J6 | 5 | | |
| H1 | OD | J3 | 4 | | |
| | OS | J6 | 5 | | |
| H3 (drops placed) | OD | J2 | 4 | | |
| | OS | J2 | 4 | | |
| H5 | OD | J2 | 4 | | |
| | OS | J2 | 4 | | |
| H8 | OD | J3 | 4 | | |
| | OS | J3 | 4 | | |

FIG. 10

COMPOSITIONS AND METHODS FOR TREATING PRESBYOPIA

PRIORITY NOTICE

The present application claims priority under 35 U.S.C. § 119(e) to U.S. Provisional Patent Application Ser. No. 62/849,728 filed on May 17, 2019, the disclosure of which is incorporated herein by reference in its entirety.

TECHNICAL FIELD OF THE INVENTION

The present invention relates in general to pharmaceutical compositions for treating eye and more specifically to pharmaceutical compositions for treating presbyopia.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Presbyopia may be a gradual and natural loss of a human (mammalian and/or vertebrate) eye's ability to focus accurately on nearby objects. Presbyopia may be the normal loss of near focusing ability of the eye that occurs with aging and that may get progressively worse with further aging. Presbyopia may be known as age-related farsightedness. In humans, presbyopia may become noticeable in the mid-40s and may continue to worsen until around age 65. Presbyopia may be caused by hardening of the lens of the eye, which may naturally occur with aging. As the lens becomes less flexible, the lens cannot as readily flex and change shape to focus on close-up (near) objects. In the U.S. there may be about three million cases per year of presbyopia.

Current treatments may include wearing corrective eyeglasses/contact lenses, undergoing refractive surgery, or getting lens implants.

There is a need in the art for a pharmaceutical composition approach to treating and/or reducing presbyopia.

It is to these ends that the present invention has been developed.

BRIEF SUMMARY OF THE INVENTION

To minimize the limitations in the prior art, and to minimize other limitations that will be apparent upon reading and understanding the present specification, the present invention describes various embodiments of compositions for treating presbyopia; and methods for compounding such formulations. In some embodiments, a given composition may comprise active pharmaceutical ingredients (APIs) of pilocarpine HCl, phenylephrine HCl, pheniramine maleate, ketorolac tromethamine, combinations thereof, and/or the like. In some embodiments, other ingredients (e.g., non-API ingredients) may comprise boric acid, polyethylene glycol (400), propylene glycol, BAK (benzalkonium chloride), combinations thereof, and/or the like. In some embodiments, the pilocarpine HCl may be present in the composition in a range of 0.1% to 2%, by weight by volume. In some embodiments, the phenylephrine HCl may be present in the composition in a range of 0.1% to 1.5%, by weight by volume. In some embodiments, the pheniramine maleate may be present in the composition in a range of 0.07% to 0.35%, by weight by volume. In some embodiments, the ketorolac tromethamine may be present in the composition in a range of 0.01% to 0.6%, by weight by volume. In some embodiments, the boric acid may be present in the composition in a range of 0.5% to 1.5%, by weight by volume. In some embodiments, the polyethylene glycol may be present in the composition in a range of 0.1% to 1%, by weight by volume. In some embodiments, the propylene glycol may be present in the composition in a range of 0.1% to 1%, by weight by volume. In some embodiments, the BAK may be present in the composition in a range of 0.005% to 0.01%, by weight by volume. In some embodiments, the solvent may be mostly (substantially) water (such as sterile water and/or WFI [water for injection or water for irrigation]).

It is an objective of the present invention to provide an effective and safe treatment for presbyopia.

It is another objective of the present invention to provide an effective and safe means for reducing presbyopia.

It is another objective of the present invention to provide a composition comprising active pharmaceutical ingredients (APIs) of: pilocarpine HCl, phenylephrine HCl, pheniramine maleate, ketorolac tromethamine, combinations thereof, and/or the like.

It is another objective of the present invention to provide a composition comprising: pilocarpine HCl, phenylephrine HCl, pheniramine maleate, ketorolac tromethamine, boric acid, polyethylene glycol (400), propylene glycol, BAK (benzalkonium chloride), combinations thereof, and/or the like.

It is another objective of the present invention to provide a composition comprising APIs of: pilocarpine HCl, phenylephrine HCl, pheniramine maleate, ketorolac tromethamine, combinations thereof, and/or the like for treating and/or reducing presbyopia.

It is another objective of the present invention to provide a composition comprising: pilocarpine HCl, phenylephrine HCl, pheniramine maleate, ketorolac tromethamine, boric acid, polyethylene glycol (400), propylene glycol, BAK, combinations thereof, and/or the like for treating and/or reducing presbyopia.

It is another objective of the present invention to provide a composition comprising APIs of: pilocarpine HCl in a range of 0.1% to 2%, by weight per volume; phenylephrine HCl in a range of 0.1% to 1.5%, by weight per volume; pheniramine maleate in a range of 0.07% to 0.35%, by weight per volume; ketorolac tromethamine in a range of 0.01% to 0.6%, by weight per volume; combinations thereof; and/or the like for treating and/or reducing presbyopia.

It is yet another objective of the present invention to provide a composition comprising pilocarpine HCl in a range of 0.1% to 2%, by weight per volume; phenylephrine HCl in a range of 0.1% to 1.5%, by weight per volume; pheniramine maleate in a range of 0.07% to 0.35%, by weight per volume; ketorolac tromethamine in a range of 0.01% to 0.6%, by weight per volume; boric acid in a range of 0.5% to 1.5%, by weight per volume; polyethylene glycol (400) in a range of 0.1% to 1%, by weight per volume; propylene glycol in a range of 0.1% to 1%, by weight per volume; BAK in a range of 0.005% to 0.01%, by weight per volume; combinations thereof; and/or the like for treating and/or reducing presbyopia.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the FIGURES (and tables) have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

REFERENCE NUMERAL SCHEDULE 100 method of compounding composition 100
101 step of prepping and cleaning work area 101
102 step of using sterilized and/or depyrogenated equipment/tools 102
103 step of weighing out ingredients 103
104 step of dissolving weighed out ingredients 104
105 step of testing and adjusting pH 105
106 step of qs to final volume 106
107 step of sterile filtering into final container 107
108 step of QA/QC testing 108
109 step of labeling and storing 109

DETAILED DESCRIPTION OF THE INVENTION

Various embodiments of the present invention may be characterized as one or more of the following: a composition for providing at least one therapeutic effect (e.g., a benefit) in a patient; a pharmaceutical composition for providing at least one therapeutic effect in the patient; an ophthalmic composition for providing at least one therapeutic effect in the patient; a topical ophthalmic composition for providing at least one therapeutic effect in the patient; an ophthalmic composition formulated for application to an eye of the patient; a method of treating a condition in the patient using the composition; a method of reducing the condition in the patient using the composition; combinations thereof; and/or the like. In some embodiments, the composition may be the pharmaceutical composition, the ophthalmic composition, the topical ophthalmic composition, combinations thereof, and/or the like. In some embodiments, the patient may be a human, a mammal, or a vertebrate.

In some embodiments, the condition may be presbyopia. In some embodiments, the at least one therapeutic effect may be reducing presbyopia. Presbyopia may be the gradual loss of the patient's eyes' ability to focus on nearby objects, often naturally related to aging. \

In some embodiments, the composition may be an eyes drop medication that may allow the adult males or females from ages of 40 to 65 regain and/or improve their near vision making them less dependent on reading glasses. In some embodiments, the composition may be an eyes drop medication that may allow the adult males or females from ages of 40 to 70 regain and/or improve their near vision making them less dependent on reading glasses.

In some embodiments, pseudophakic patients, regardless of age, may benefit from the composition.

In some embodiments, the composition may improve reading vision through pharmalogic effects of reestablishing some accommodation in the eye and miosis of the pupil. The mechanism of accommodation may allow the treated eye to regain flexibility of the intraocular lens found in younger patients. The mechanism of miosis may allow the pupil size to become just slightly smaller than the normal/typical physiologic pupil size. The pupil may be like an aperture of a camera and a smaller pupil size may allow the eye to regain a greater depth of field of vision allowing greater near vision without compromising distance vision.

In some embodiments, compositions disclosed herein may be used to treat and/or reduce refractive error for patients with hyperopia (including, but not limited, to children), up to +4.00 diopters.

In some embodiments, because of a pinhole effect of the compositions described herein, when administered as drops to the given eye, the given composition may improve distance visual acuity in patients with certain corneal diseases that leave patients with higher order aberrations causing glare and halos. These patients may be post Lasik patients (or the like) and/or post cataract surgery patients who have monofocal or multifocal or accomadative iols.

Patients who have had corneal surgery (such as, but not limited to, LASIK, PRK, SMILE, corneal inlays, Intacs, cornea transplants [e.g., PKP, DESK, DMEK, and/or the like], cross-linking, and/or the like) and patients with severe dry eye may benefit from eye drops treatment of the compositions disclosed herein.

In some embodiments, the composition may comprise at least one active pharmaceutical ingredient (API). In some embodiments, the at least one API may be selected from: at least one chemical that may stimulate cholinergic receptors causing miosis (such as, but not limited to, pilocarpine HCl); at least one direct acting alpha adrenergic agonist (such as, but not limited to, phenylephrine HCl); at least one vasoconstrictor (such as, but not limited to, phenylephrine HCl); at least one histamine inhibitor (such as, but not limited to, pheniramine maleate); at least one smooth muscle contractor (such as, but not limited to, pheniramine maleate); at least one vasodilator (such as, but not limited to, pheniramine maleate); at least one NSAID (such as, but not limited to, ketorolac tromethamine); at least one anti-inflammatory agent (such as, but not limited to, ketorolac tromethamine); at least one prostaglandin synthesis inhibitor (such as, but not limited to, ketorolac tromethamine); combinations thereof; and/or the like.

In some embodiments, the at least one API may be selected from: pilocarpine, phenylephrine HCL, ketorolac tromethamine, pheniramine maleate, salts thereof, combinations thereof, and/or the like.

In some embodiments, the composition may comprise the APIs of: pilocarpine, phenylephrine HCL, ketorolac tromethamine, pheniramine maleate, salts thereof, combinations thereof, and/or the like.

In some embodiments, the composition may comprise the APIs of: pilocarpine in a range of 0.1% to 2%; phenylephrine HCL in a range of 0.1% to 1.5%; ketorolac tromethamine in a range of 0.01% to 0.6%; and pheniramine maleate in a range of 0.07% to 0.35%—with respect to weight by volume, in an overall solvent of water.

In some embodiments, the composition may comprise other ingredients, such as, but not limited to, boric acid, polyethylene glycol (400), propylene glycol, benzalkonium chloride (BAK), sodium hydroxide, combinations thereof, and/or the like. In some embodiments, these other ingredients may be non-APIs.

In some embodiments, the composition may comprise the following ingredients: pilocarpine in a range of 0.1% to 2%; phenylephrine HCL in a range of 0.1% to 1.5%; ketorolac tromethamine in a range of 0.01% to 0.6%; pheniramine maleate in a range of 0.07% to 0.35%; boric acid in a range of 0.5% to 1.5%; polyethylene glycol (400) in a range of 0.1% to 1%; propylene glycol in a range of 0.1% to 1%; and benzalkonium chloride in a range of 0.005% to 0.01%—with respect to weight by volume, in an overall solvent of water.

In some embodiments, the composition may have a pH of 6.39 to 6.51. In some embodiments, the composition may have a pH of 5.5 to 7.5.

In some embodiments, the composition may be sterile filtered. In some embodiments, the composition may be pushed through a 0.2 micro filter.

In some embodiments, the composition may be stored at room temperature. In some embodiments, the composition may be stored at room temperature for about 180 days (wherein "about" may plus or minus two days). In some embodiments, the composition may be stored at temperatures from about 68 degrees to about 77 degrees Fahrenheit (wherein "about" may be plus or minus two degrees Fahrenheit).

In some embodiments, the composition should be protected from light and from excessive heat. In some embodiments, the composition should not be used if brown in appearance and/or if contains precipitates.

In some embodiments, pilocarpine HCl (hydrogen chloride) may be an API in the composition. In some embodiments, pilocarpine HCl may stimulates cholinergic receptors causing miosis. In some embodiments, pilocarpine HCl may be present in the composition in a range of 0.1% to 2%, weight by volume. In some embodiments, pilocarpine HCl may be present in the composition in a range of 0.25% to 35%, weight by volume.

In some embodiments, phenylephrine HCl may be an API in the composition. In some embodiments, phenylephrine HCl may be a direct acting alpha adrenergic agonist causing vasoconstriction. In some embodiments, the phenylephrine HCl may be a directly acting sympathmimetic agent (e.g., with a-adrenergic effects) used in the eye as a mydriatic agent (e.g., to dilate the eye's pupil). In the eye, phenylephrine HCl may constrict ophthalmic blood vessels and the radial muscle of the iris. In some embodiments, phenylephrine HCl may be present in the composition in a range of 0.1% to 1.5%, weight by volume.

In some embodiments, pheniramine maleate may be an API in the composition. In some embodiments, pheniramine maleate may inhibit histamine. In some embodiments, pheniramine maleate may facilitate smooth muscle contraction and/or vasodilation. In some embodiments, pheniramine maleate may be present in the composition in a range of 0.07% to 0.35%, weight by volume.

In some embodiments, ketorolac tromethamine may be an API in the composition. In some embodiments, the ketorolac tromethamine may also be known as ketorolac, ketorolac tromethamine ophthalmic solution, and ketorolac tromethamine injection. In some embodiments, ketorolac tromethamine may be a NSAID (a nonsteroidal anti-inflammatory drug). In some embodiments, the ketorolac tromethamine may be a non-steroidal anti-inflammatory drug (NSAID), in the family of heterocyclic acetic acid derivatives. In some embodiments, ketorolac tromethamine may be an anti-inflammatory agent. In some embodiments, ketorolac tromethamine may inhibit prostaglandin synthesis. In some embodiments, ketorolac tromethamine may inhibit prostaglandin synthesis by decreasing the activity of cyclo-oxygenase. Mechanism of action for ketorolac tromethamine may be through inhibition of prostaglandin synthesis secondary to inhibition of COX (cyclooxygenase) production; wherein COX inhibition may be nonselective. In some embodiments, the ketorolac tromethamine may be used as an analgesic. In some embodiments, ketorolac tromethamine may be used to treat inflammation in the eye, at the eye, and/or around the eye. In some embodiments, ketorolac tromethamine may be sued to treat eye inflammation post eye surgery. In some embodiments, ketorolac tromethamine may be used to during eye surgery, during an intraocular ophthalmic procedure, and/or before an intraocular procedure in preparation for that procedure. In some embodiments, ketorolac tromethamine may be present in the composition in a range of 0.01% to 0.6%, weight by volume.

In some embodiments, the composition may also comprise boric acid or the like. Boric acid may be a non-API in the composition. In some embodiments, boric acid may be used in the composition to adjust tonicity. In some embodiments, boric acid may be used in the composition as a preservative. In some embodiments, boric acid may be used in the composition to adjust tonicity and/or as a preservative. In some embodiments, the boric acid may be a weak acid. In some embodiments, the boric acid may have mild antibiotic properties and/or antifungal properties; and thus, act as a preservative. Boric acid solutions may be used to cleanse and/or irrigate eyes (e.g., helping to remove irritants and/or pollutants from the eyes). Boric acid solutions may provide soothing relief to eye irritation. In some embodiments, the boric acid may be present in the composition in a range of 0.5% to 1.5%, weight by volume.

In some embodiments, the composition may also comprise polyethylene glycol 400 or the like. Polyethylene glycol 400 may be a non-API in the composition. In some embodiments, polyethylene glycol 400 may be sued in the composition to enhance the aqueous solubility or dissolution characteristics of aqueous poorly soluble ingredients. In some embodiments, the polyethylene glycol 400 may be present in the composition in a range from 0.1% to 1%, weight by volume.

In some embodiments, the composition may also comprise propylene glycol or the like. Propylene glycol may be a non-API in the composition. In some embodiments, propylene glycol may be used as a solvent, extractant, and/or as a preservative. In some embodiments, propylene glycol may be present in the composition in a range of 0.1% to 1%, weight by volume.

In some embodiments, the composition may also comprise benzalkonium chloride (BAK) or the like. BAK may be a non-API in the composition. In some embodiments, BAK may be a detergent, a quaternary ammonium compound with a broad range of antimicrobial activity. In some embodiments, BAK may be a preservative in the composition. In some embodiments, BAK may be an antimicrobial preservative in the composition. In some embodiments, BAK may be used as an antiseptic in the composition. In some embodiments, BAK may be used as a disinfectant in the composition. In some embodiments, BAK may be used as a solubilizing agent in the composition. In some embodiments, BAK may be used as a wetting agent in the composition. In some embodiments, BAK may be used as one or more of a detergent, preservative, antimicrobial preservative, antiseptic, disinfectant, solubilizing agent, wetting agent, combinations thereof, and/or the like in the composition. In some embodiments, BAK may be present in the composition in a range of 0.005% to 0.01%, weight by volume.

In some embodiments, the composition may be BAK free. In some embodiments, the composition may be free of BAK or the like.

In some embodiments, the composition may be substantially free of preservatives.

In some embodiments, a pH of the composition may be adjusted by sodium hydroxide (NaOH). In some embodiments, NaOH may be used to adjust a pH of the composition to a pH of 6.39 to 6.51. In some embodiments, NaOH may be used to adjust a pH of the composition to a pH 5.5 to 7.5. Since the composition may be mostly water, NaOH in solution may dissociate into its component ions.

In some embodiments, a carrier and/or a solvent of the composition may be mostly (and/or substantially) water. In some embodiments, this water may be purified water, reverse osmosis (RO) generated water, deionized (DI) water, sterile water, water for injection (WFI), and/or water for irrigation (WFI). WFI may be sterile water that may be substantially free of pyrogens.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

Figure 1:
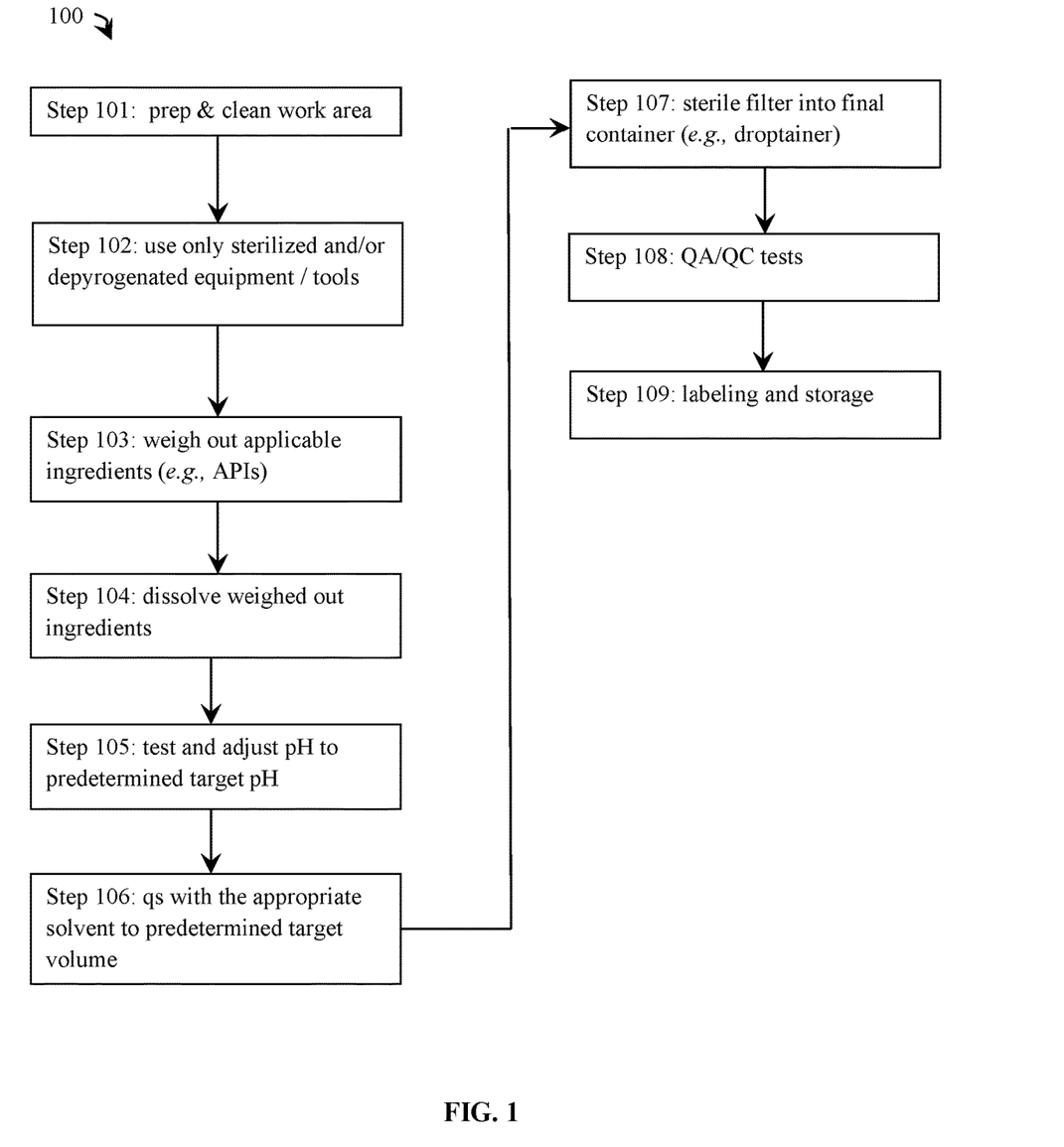
FIG. 1 depicts a flow diagram showing at least some steps of a method of compounding a composition.
Figure 2:
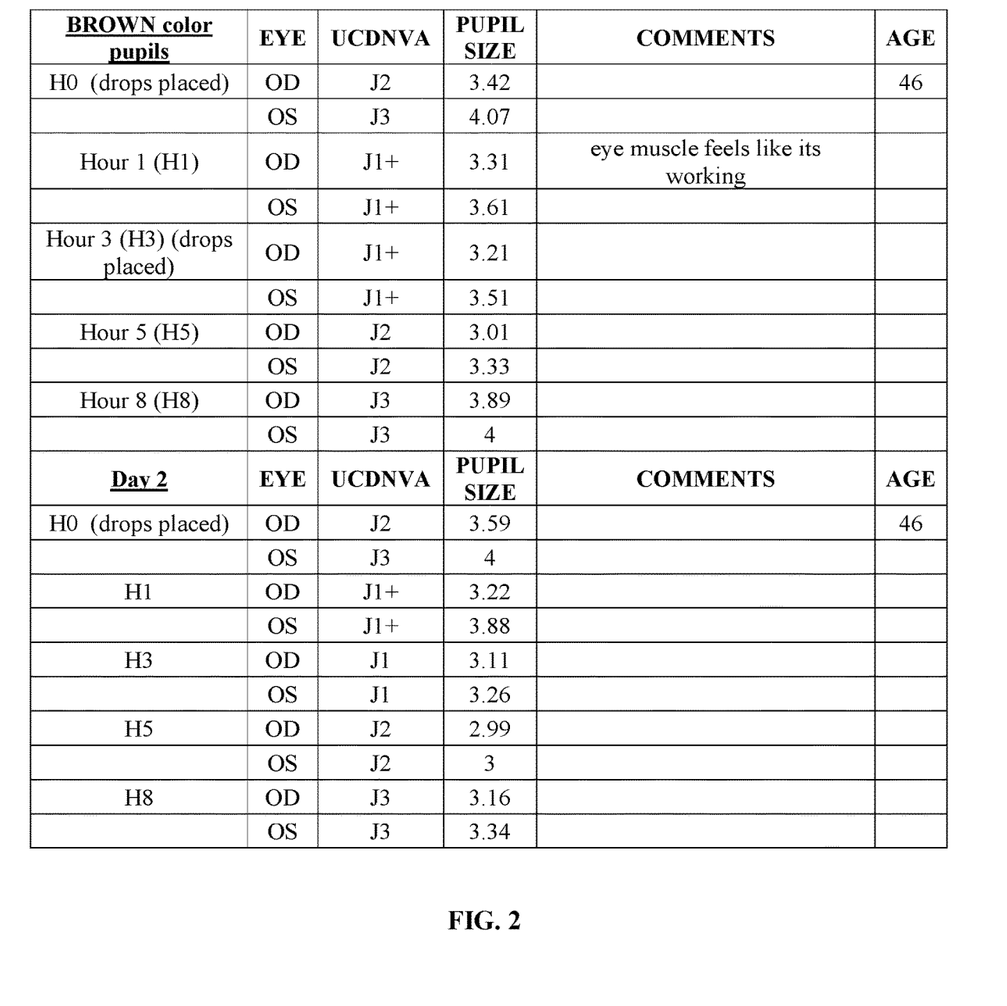
FIG. 2 shows patient one study data.
Figure 3:
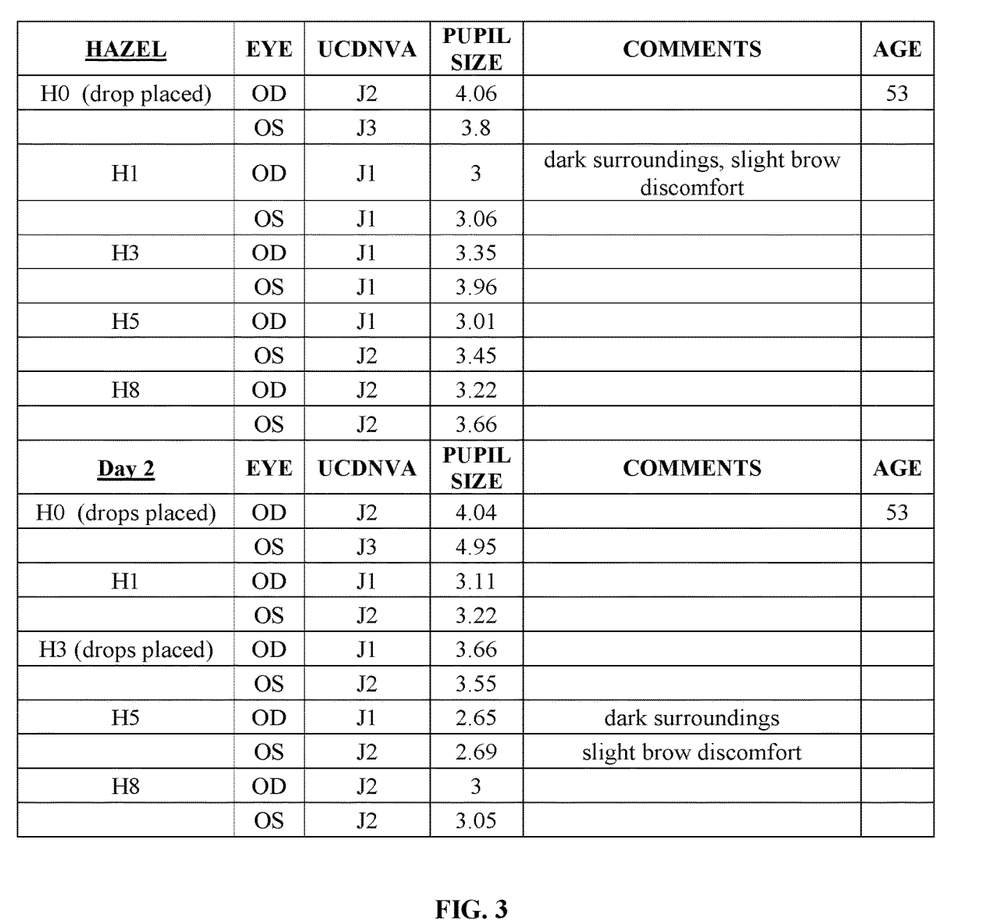
FIG. 3 shows patient two study data.
Figure 4:
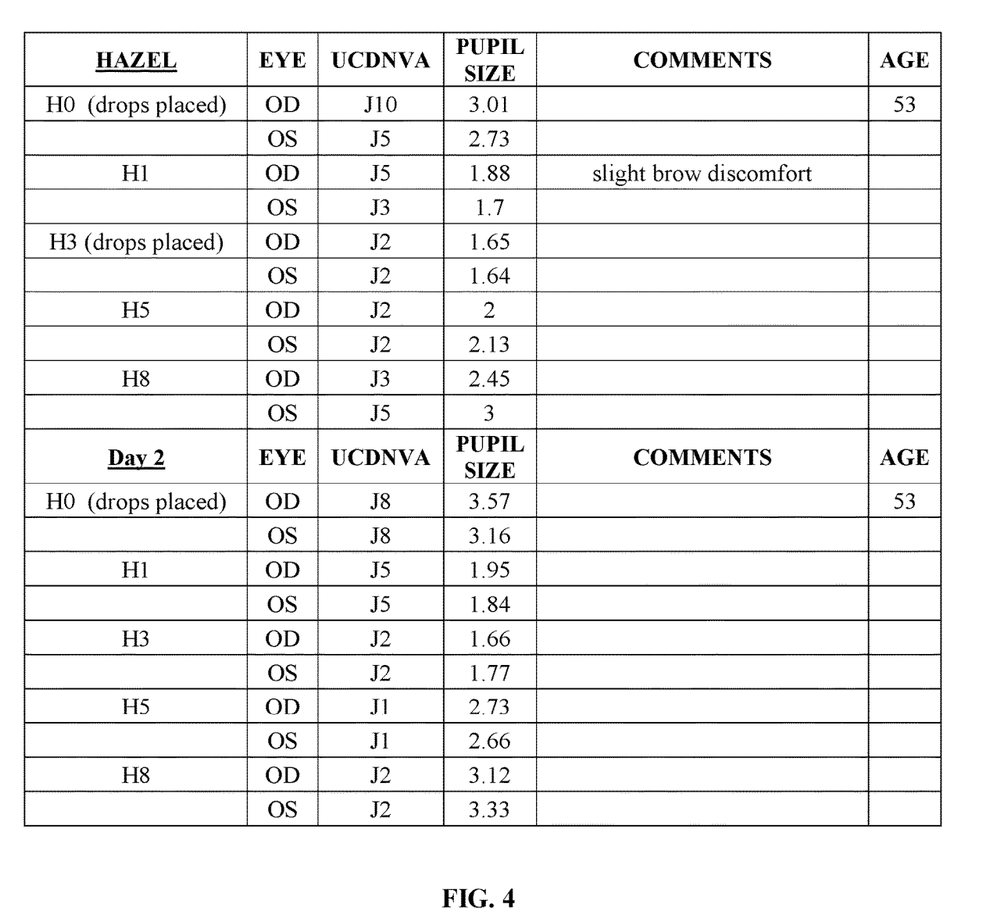
FIG. 4 shows patient three study data.
Figure 5:
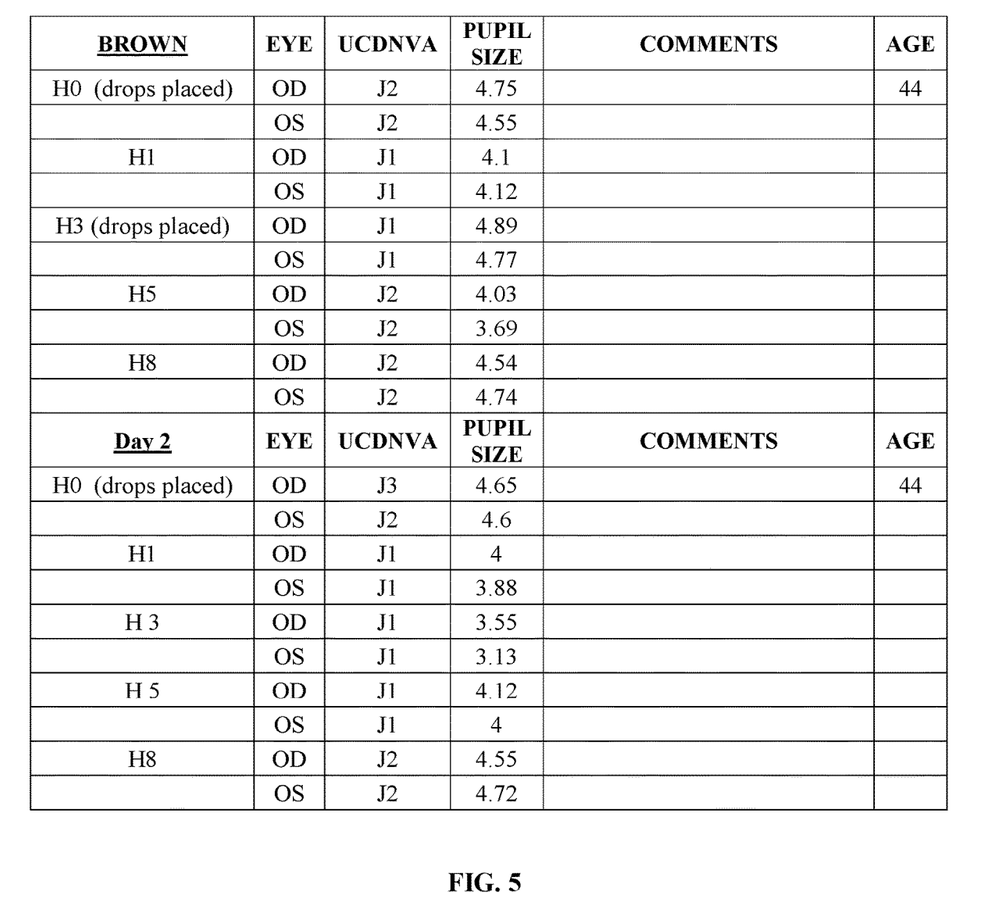
FIG. 5 shows patient four study data.
Figure 6:
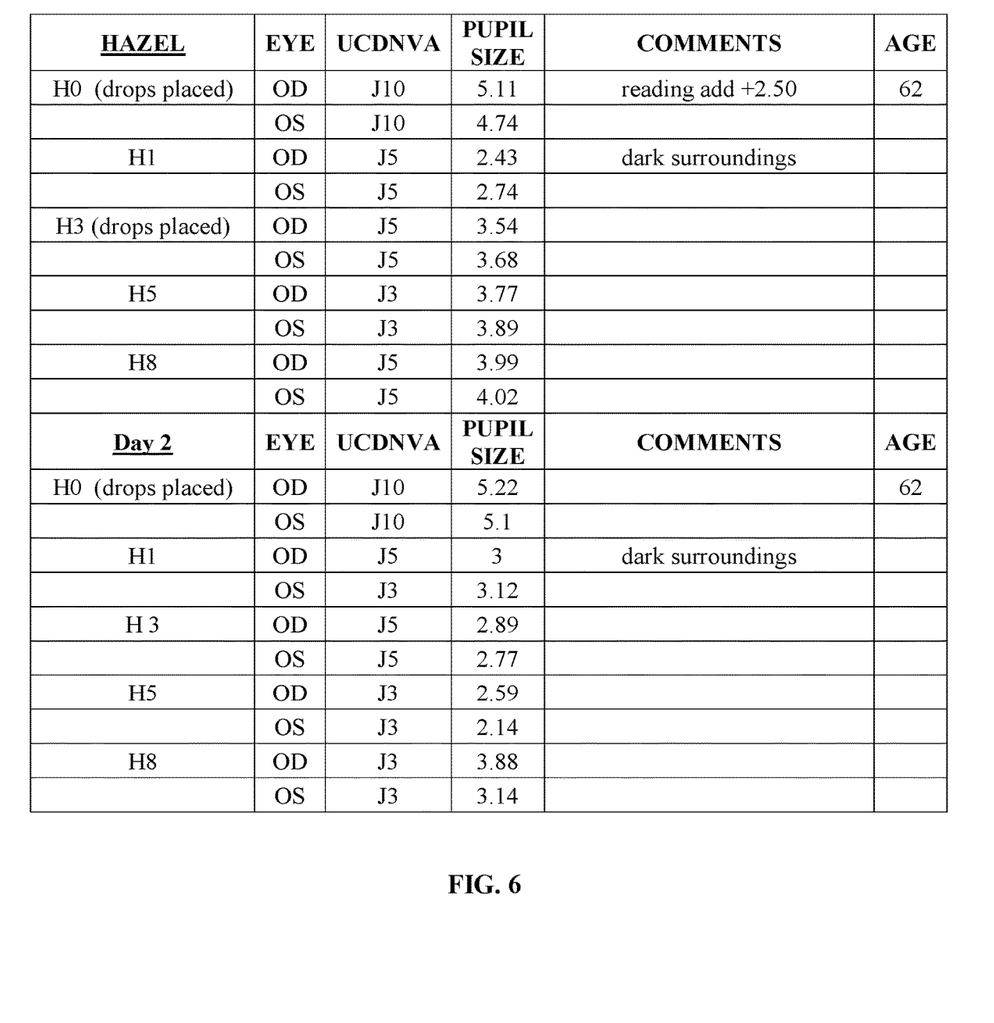
FIG. 6 shows patient five study data.
Figure 7:
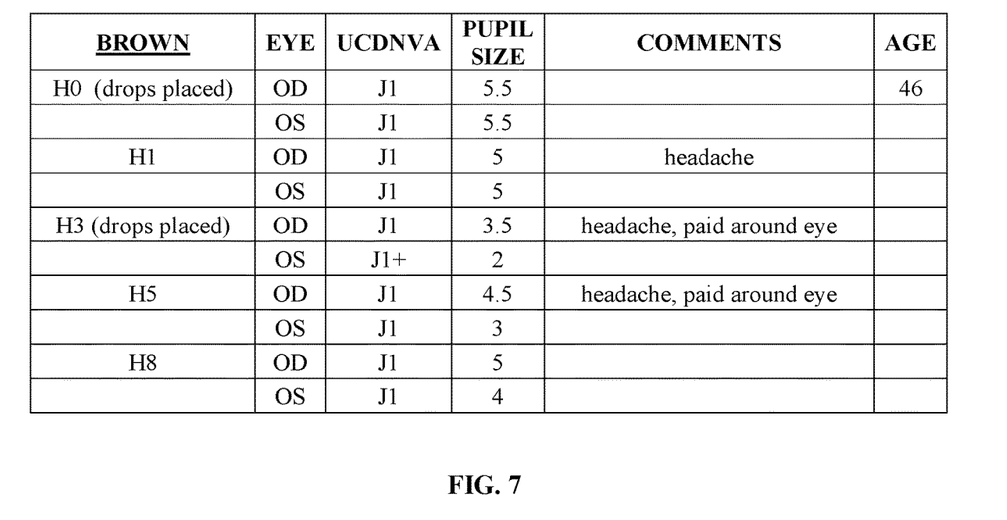
FIG. 7 shows patient six study data.
Figure 8:
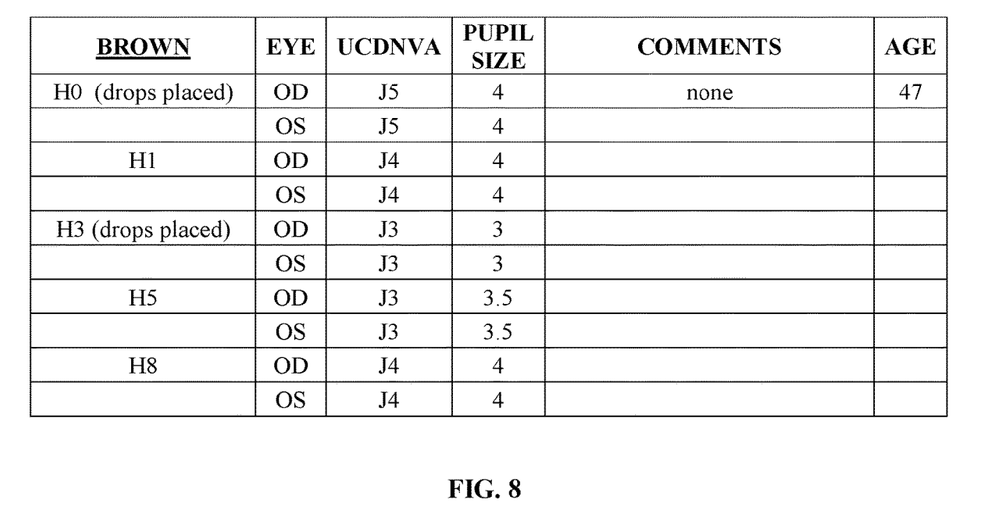
FIG. 8 shows patient seven study data.
Figure 9:
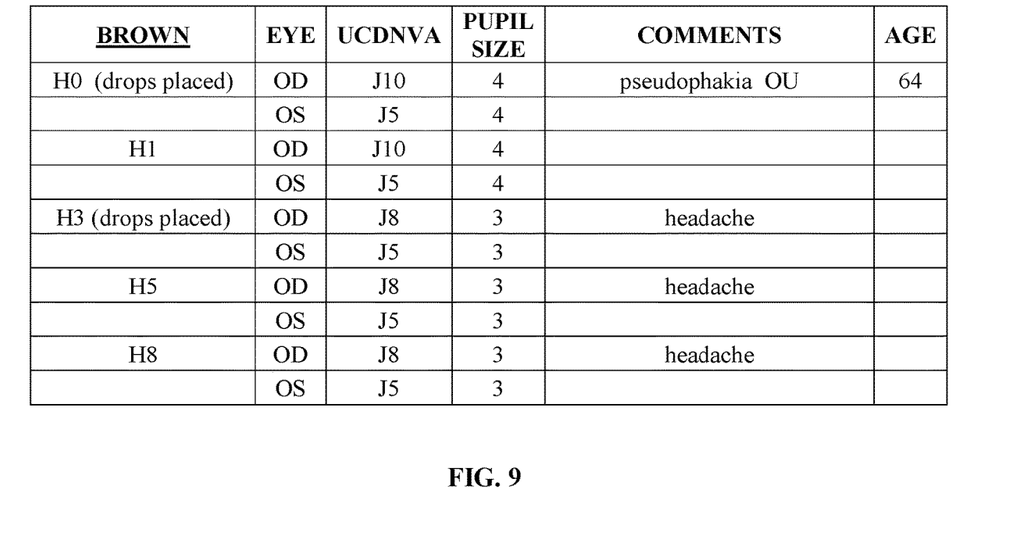
FIG. 9 shows patient eight study data.
Figure 10:
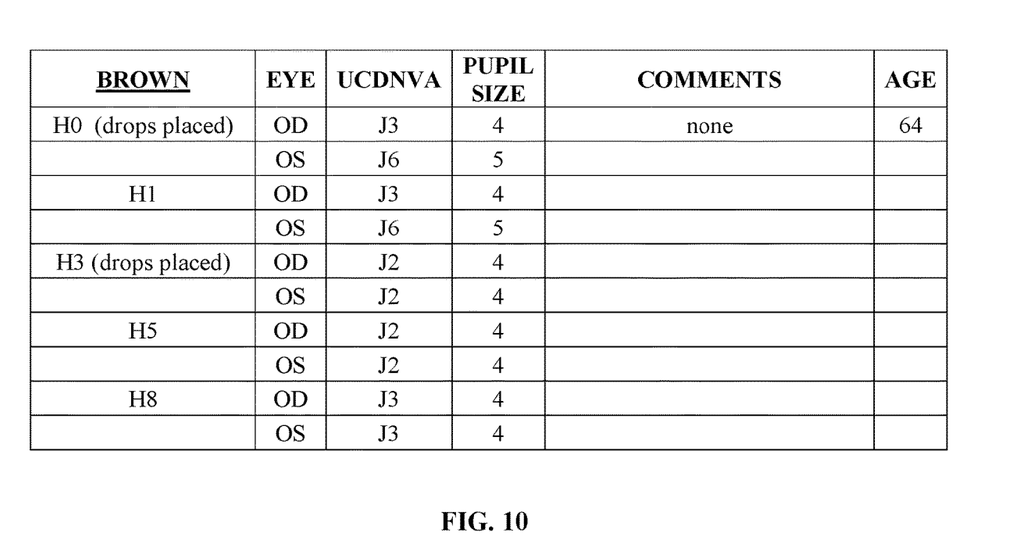
FIG. 10 shows patient nine study data.

FIG. 1 may depict a flow diagram of a method 100; wherein method 100 may comprise the steps for compounding and/or filling a given composition disclosed herein. In some embodiments, method 100 may comprise steps of: step 101, step 102, step 103, step 104, step 105, step 106, step 107, step 108, and step 109.

Continuing discussing FIG. 1, in some embodiments, step 101 may be a step of prepping a clean work area (e.g., cleaning and/or disinfecting the work area). In some embodiments, the work area may be a work surface within a clean room; a laminar airflow hood; powder hood; compounding aseptic isolator (CAI); combinations thereof; and/or the like. In some embodiments, step 101 may progress into step 102.

Continuing discussing FIG. 1, in some embodiments, step 102 may be a step of (prepping and) using only sterilized and/or depyrogenated equipment, tools, and/or surfaces of equipment and/or tools. In some embodiments, such equipment and/or tools may be: gloves; beakers; mixing vessels (compounding vessels); scale receiving surfaces (e.g., for receiving weighted out ingredients); spatulas; pH meter (probe); pumps (e.g., for pushing solution through 0.2 micro filters); tubing, 0.2 micron filters; filter integrity test equipment (bubble point testing equipment); filing machines; final storage container (such as, but not limited, droptainers); and/or the like. In some embodiments, step 102 may progress into step 103.

Continuing discussing FIG. 1, in some embodiments, step 103 may be a step of weighing out the applicable ingredients (such as, but not limited to APIs and non-APIs). In some embodiments, step 103 may be carried out on a work surface within a clean room; in a laminar airflow hood; powder hood; in compounding aseptic isolator (CAI); combinations thereof; and/or the like. In some embodiments, one or more scales may be used in step 103. In some embodiments, weighted out ingredients may be added to one or more beakers and/or mixing vessels (compounding vessels). In some embodiments, step 103 may progress into step 104.

Continuing discussing FIG. 1, in some embodiments, step 104 may be a step of dissolving the weighed out ingredients (e.g., in powder, crystal, granule, pellet, or the like form) into an appropriate solvent/carrier, such as, but not limited to aqueous solutions, including, but not limited to, sterile water (or WFI). In some embodiments, step 104 may involve taring out a receiving vessel (e.g., a beaker), filing that receiving vessel to about 80% of total expected volume for a given batch with the appropriate solvent/carrier (e.g., sterile water and/or WFI), and then adding in the weighted out ingredients to that receiving vessel and dissolving into solution within that receiving vessel. In some embodiments, in step 104, the weighted out ingredients may be added to the receiving vessel in the following order: pilocarpine HCl, phenylephrine HCl, boric acid, polyethylene glycol (400), propylene glycol, pheniramine maleate, ketorolac tromethamine, and lastly BAK; and further, step 104 may require that each such ingredient is substantially to completely dissolved before adding in the next such ingredient. In some embodiments, step 104 may progress into step 105.

Continuing discussing FIG. 1, in some embodiments, step 105 may be a step of testing (e.g., via a calibrated pH meter) and adjusting (e.g., via adding acids and/or bases) to a pH of a predetermined target value. For example, and without limiting the scope of the present invention, 5% NaOH may be added to the resulting solution of step 104 to bring the pH into a range of 6.51 to 6.39. In some embodiments, a final target pH of the composition may be a pH of 6.39 to 6.51. In some embodiments, a final target pH of the composition may be a pH of 5.5 to 7.5. In some embodiments, step 105 may progress into step 106.

Continuing discussing FIG. 1, in some embodiments, step 106 may be a step of qs ("quantity sufficient") with the appropriate solvent/carrier (e.g., the sterile water (or the WFI)). That is, step 106 may be a step of adding the appropriate solvent/carrier so the total expected volume of this batch is on target. In some embodiments, step 106 may progress into step 107.

Continuing discussing FIG. 1, in some embodiments, step 107 may be a step of sterile filtering (e.g., a 0.22 micron filter) the resulting solution from step 106 (or step 105) to yield the given composition. In some embodiments, step 107 may be a step of sterile filtering (e.g., a 0.22 micron filter) the resulting solution from step 106 (or step 105) into the final storage containers, such as, but not limited to, (sterile) droptainers. In some embodiments, the final storage container may be one or more of: sterile ophthalmic dropper bottles (e.g., a "drop-tainers," "droptainer," "steri-droppers," or the like), vials, pre-filled syringes, and/or the like. In some embodiments, step 107 may progress into step 108.

Continuing discussing FIG. 1, in some embodiments, step 108 may be a step of QA/QC (quality assurance/quality control) testing, such as bubble point testing (filter integrity testing), stability testing, potency testing, sterility testing, pyrogen testing, endotoxin testing, clarity testing, color comparison testing, combinations thereof, and/or the like. In some embodiments, some QA/QC testing may be done on solutions (e.g., samples from) from step 104, 105, 106, and/or 107. In some embodiments, step 108 may progress into step 109.

Continuing discussing FIG. 1, in some embodiments, step 109 may be a step of labeling (e.g., contents, expiration date, lot number, compounding date, and/or the like) and/or storage.

In some embodiments, method 100 may comprise one or more steps from FIG. 1. In some embodiments, at least some steps shown in FIG. 1 may be omitted in method 100. In some embodiments, at least some steps shown in FIG. 1 may be performed out of the shown order.

In some embodiments, a predetermined amount of the composition may be filled into the final storage container that is intended to be used by a patient and/or to be used by one administering the composition to the patient. In some embodiments, the final storage container may be one or more of: sterile ophthalmic dropper bottles (e.g., a "droptainers," "droptainer," "steri-droppers," or the like), vials, pre-filled syringes, and/or the like. In some embodiments, the sterile ophthalmic dropper bottles be sterilized. In some embodiments, the bottle or vial portion of the sterile ophthalmic dropper bottle may be substantially constructed from polyethylene or the like. In some embodiments, the dropper portion of the sterile ophthalmic dropper bottle may be substantially constructed from polypropylene or the like. In some embodiments, plastics used in the sterile ophthalmic dropper bottles may be substantially zinc stearate-free, which in turn may minimize precipitate/particulate formation in the sterile ophthalmic dropper bottles. In some embodiments, the sterile ophthalmic dropper bottles may have fixed and predetermined sizes; such as, but not limited to, volumes of 3 mL (milliliters), 7 mL, 10 mL, and 15 mL.

In some embodiments, drop(s) from a given ophthalmic dropper bottle, with an appropriate volume of the composition, may be administered to the eye of the patient, by dropping the drop(s) into the eye of the patient. In some embodiments, the composition may be dosed qd-qid. In some embodiments, the composition may be applied by dropping a drop of the composition into the eye of the patient from once per day up to four times per day. In some embodiments, the composition may be applied by dropping a drop of the composition into the eye of the patient from once per day up to six times per day.

In one study of nine patients, of seven females and two males, the composition, in eye drop form, was used to treat the eyes of these nine patients. These patients were between the ages of 44 to 64 years. There were both brown and blue eyes in this study population. Five of the patients were followed (observed) for two days and one of the patients was psusdophakic and had already had cataract surgery.

Tables 1 through 9 (includes in the accompanying drawing FIGURES) show the patient study data, with each of the nine tables being for one of the nine patients.

These nine patients instilled the composition at the first-time measurement H0 (hour zero) and at H3 (hour three) (i.e., were dosed twice in a day) and had their near vision checked several times through an eight hour time period. All the patients noticed improvement in reading vision and were noted having smaller pupil sizes. The patients regained a range of one to eight lines of greater reading vision. Patients with worse overall reading vision tended to show greater improvement. Reading vision was measured on the Jeager near vision scale. Some patients improved from j2 to j1+an improvement of three lines of vision. Some patients improved from j10-j2 an improvement of eight lines.

In this cohort of patients, the greatest improvement in reading vision usually occurred between three to five hours after the eye drops of the composition were used in the treated eyes. The affects began to wear off after about eight hours after the composition eye drops were used. All the patients felt less dependent on reading glasses after the patients' eyes were treated with the composition.

Compositions and methods for treating presbyopia have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method for reducing presbyopia in an eye of a human, the method comprising administering to the eye of the human an aqueous ophthalmic composition comprising pilocarpine hydrochloride, phenylephrine hydrochloride, pheniramine maleate, and ketorolac tromethamine as active pharmaceutical ingredients.

2. The method according to claim 1, wherein the aqueous ophthalmic composition comprises:
   (i) pilocarpine hydrochloride at a concentration in the range of 0.10% w/v to 2.00% w/v;
   (ii) phenylephrine hydrochloride at a concentration in the range of 0.10% w/v to 1.50% w/v;
   (iii) pheniramine maleate at a concentration in the range of 0.07% w/v to 0.35% w/v; and
   (iv) ketorolac tromethamine at a concentration in the range of 0.01% w/v to 0.60% w/v.

3. The method according to claim 1, wherein the aqueous ophthalmic composition further comprises boric acid, polyethylene glycol, propylene glycol, and benzalkonium chloride.

4. The method according to claim 3, wherein the aqueous ophthalmic composition comprises:
   (i) boric acid at a concentration in the range of 0.50% w/v to 1.50% w/v;
   (ii) polyethylene glycol at a concentration in the range of 0.10% w/v to 1.00% w/v;
   (iii) propylene glycol at a concentration in the range of 0.10% w/v to 1.00% w/v; and
   (iv) benzalkonium chloride at a concentration in the range of 0.005% w/v to 0.010% w/v.

5. The method according to claim 4, wherein the aqueous ophthalmic composition comprises:
   (i) pilocarpine hydrochloride at a concentration in the range of 0.10% w/v to 2.00% w/v;
   (ii) phenylephrine hydrochloride at a concentration in the range of 0.10% w/v to 1.50% w/v;
   (iii) pheniramine maleate at a concentration in the range of 0.07% w/v to 0.35% w/v; and
   (iv) ketorolac tromethamine at a concentration in the range of 0.01% w/v to 0.60% w/v.

6. The method according to claim 1, wherein the aqueous ophthalmic composition has a pH in the range of 5.50 to 7.50.

7. The method according to claim 1, wherein the aqueous ophthalmic composition has a pH in the range of 6.39 to 6.51.

8. An ophthalmic dropper bottle comprising an aqueous ophthalmic composition comprising pilocarpine hydrochloride, phenylephrine hydrochloride, pheniramine maleate, and ketorolac tromethamine.

9. The ophthalmic dropper bottle according to claim 8, wherein the aqueous ophthalmic composition comprises:
   (i) pilocarpine hydrochloride at a concentration in the range of 0.10% w/v to 2.00% w/v;
   (ii) phenylephrine hydrochloride at a concentration in the range of 0.10% w/v to 1.50% w/v;
   (iii) pheniramine maleate at a concentration in the range of 0.07% w/v to 0.35%, by weight by volume w/v; and
   (iv) ketorolac tromethamine at a concentration in the range of 0.01% w/v to 0.60% w/v.

10. The ophthalmic dropper bottle according to claim 8, wherein the aqueous ophthalmic composition further comprises boric acid, polyethylene glycol, propylene glycol, and benzalkonium chloride.

11. The ophthalmic dropper bottle according to claim 10, wherein the aqueous ophthalmic composition comprises:
   (i) boric acid at a concentration in the range of 0.50% w/v to 1.50% w/v;
   (ii) polyethylene glycol at a concentration in the range of 0.10% w/v to 1.00% w/v;
   (iii) propylene glycol at a concentration in the range of 0.10% w/v to 1.00% w/v; and
   (iv) benzalkonium chloride at a concentration in the range of 0.005% w/v to 0.010% w/v.

12. The ophthalmic dropper bottle according to claim 11, wherein the aqueous ophthalmic composition comprises:
   (i) pilocarpine hydrochloride at a concentration in the range of 0.10% w/v to 2.00% w/v;
   (ii) phenylephrine hydrochloride at a concentration in the range of 0.10% w/v to 1.50% w/v;
   (iii) pheniramine maleate at a concentration in the range of 0.07% w/v to 0.35% w/v; and
   (iv) ketorolac tromethamine at a concentration in the range of 0.01% w/v to 0.60% w/v.

13. The ophthalmic dropper bottle according to claim 8, wherein the aqueous ophthalmic composition has a pH in the range of 5.50 to 7.50.

14. The ophthalmic dropper bottle according to claim 8, wherein the aqueous ophthalmic composition has a pH in the range of 6.39 to 6.51.

15. The ophthalmic dropper bottle according to claim 8, wherein the aqueous ophthalmic composition reduces presbyopia in the eye of a human.

* * * * *